(12) United States Patent
Quax et al.

(10) Patent No.: US 6,506,579 B1
(45) Date of Patent: Jan. 14, 2003

(54) INCREASING PRODUCTION OF PROTEINS IN GRAM-POSITIVE MICROORGANISMS USING SECG

(75) Inventors: Wilhelmus J. Quax, Vorschooten (NL); Robert M. Caldwell, Belmont, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 09/462,843

(22) PCT Filed: Jul. 14, 1998

(86) PCT No.: PCT/US98/14648

§ 371 (c)(1),
(2), (4) Date: Mar. 22, 2000

(87) PCT Pub. No.: WO99/04006

PCT Pub. Date: Jan. 28, 1999

(30) Foreign Application Priority Data

Jul. 15, 1997 (EP) ............................................. 97305228

(51) Int. Cl.$^7$ ................................................ C12P 12/06

(52) U.S. Cl. ................ 435/69.1; 435/320.1; 435/252.3; 435/252.31

(58) Field of Search ...................... 536/23.1; 435/320.1, 435/252.3, 252.31, 69.1

(56) References Cited

U.S. PATENT DOCUMENTS

| | | | |
|---|---|---|---|
| 3,817,837 A | 6/1974 | Rubenstein et al. | 195/103.5 |
| 3,850,752 A | 11/1974 | Schuurs et al. | 195/103.5 |
| 3,939,350 A | 2/1976 | Kronick et al. | 250/365 |
| 3,996,345 A | 12/1976 | Ullman et al. | 424/12 |
| 4,275,149 A | 6/1981 | Litman et al. | 435/7 |
| 4,277,437 A | 7/1981 | Maggio | 422/61 |
| 4,366,241 A | 12/1982 | Tom et al. | 435/7 |
| 4,816,567 A | 3/1989 | Cabilly et al. | 530/387 |

FOREIGN PATENT DOCUMENTS

WO    WO 94/19471    9/1974

OTHER PUBLICATIONS

Kunst et al. The complete genome sequence of the Gram–positive bacterium *Bacillus subtilis*. Nature. Nov., 1997. 390:249–256.* van Wely et al. Functional Identification of the Product of the *Bacillus subtilis* yvaL Gene as a SecG Homologue. J. of Bacteiiology Mar. 1999. 181(6):1786–1792.*

Ausubel et al., ed. *Current Protocols in Molecular Biology*, John Wiley & Sons, Inc. Ch. 2 and 3, 1987.

Bakhiet et al., "Studies on Transfection and Transformation of Protoplasts of *Bacillus larvae*, *Bacillus subtilis*, and *Bacillus popilliae*," *Applied and Environmental Microbiology*, vol. 49, No. 3, pp. 577–581, Mar., 1985.

Benton et al., "Steering λgt Recombinant Clones by Hybridization to Single Plaques in situ," *Science*, vol. 196, No. 4286, pp. 180–182, Apr. 8, 1977.

Chang et al., "High Frequency Transformation of *Bacillus subtilis* Protoplasts by Plasmid DNA," *Molec. Gen. Genet.*, vol. 168, pp. 111–115, 1979.

Contente et al., "Marker Rescue Transformation by Linear Plasmid DNA in *Bacillus subtilis*," *Plasmid*, vol. 2, pp. 555–571, 1979.

Diderichsen et al., "A Useful Cloning Vector for *Bacillus subtilis*," *Plasmid*, vol. 30, pp. 312–315, 1993.

Fischer et al., "Introduction of plasmid pC194 into Bacillus thuringiensis by Protoplast transformation and plasmid transfer," *Archives of Microbiology*, vol. 139, pp. 213–217, 1984.

Grunstein et al., "Colony hybridization: A method for the isolation of cloned DNAs that contain a specific gene," *Proc. Nat. Acad. Sci. USA*, vol. 72, No. 10, pp. 3961–3965, Oct., 1975.

Haima, Peter et al., "Novel plasmid marker rescue transformation system for molecular cloning in *Bacillus subtilis* enabling direct selection of recombinants," *Mol. Gen. Genet.*, vol. 223, pp. 185–191, 1990.

Holubova et al., "Transfer of Liposome–Encapsulated Plasmid DNA to *Bacillus subtilis* Protoplasts and Calcium–Treated *Escherichia coli* Cells," *Folia Microbiol.*, vol. 30, pp. 97–100, 1985.

Kok et al., "Construction of Plasmid Cloning Vectors for Lactic Streptococci Which Also Replicate in *Bacillus subtilis* and *Escherichia coli*," *Applied and Environmental Microbiology*, vol. 48, No. 4, pp. 726–731, Oct. 1984.

Kroll et al., "A Multifunctional Prokaryotic Protein Expression System: Overproduction, Affinity Purification, and Selective Detection," *DNA and Cell Biology*, vol. 12, No. 5, pp. 441–453, 1993.

Maddox et al., "Elevated Serum Levels in Human Pregnancy of a Molecule Immunochemically Similar to Eosinophil Granule Major Basic Protein," *J. Exp. Med.*, vol. 158, pp. 1211–1226, Oct. 1983.

Mann et al., "Transformation of Bacillus spp.: an Examination of the Transformation of Bacillus Protoplasts by Plasmids pUB110 and pHV33," *Current Microbiology*, vol. 13, pp. 191–195, 1986.

McDonald et al., "Plasmid Transformation of *Bacillus sphaericus* 1593," *Jouranl of General Microbiology*, vol. 130, pp. 203–208, 1984.

Murray et al., "Codon usage in plant genes," *Nucleic Acids Research*, vol. 17, No. 2, pp. 477–498, 1989.

(List continued on next page.)

*Primary Examiner*—Ponnathapu Achutamurthy
*Assistant Examiner*—Kathleen Kerr
(74) *Attorney, Agent, or Firm*—Genencor International, Inc

(57) ABSTRACT

The present invention relates to secretion in Gram-positive microorganisms. The present invention provides the nuclei acid and amino acid sequences for the *Bacillus subtilis* secretion factor SecG. The present invention also provides means for increasing the secretion of heterologous or homologous proteins in gram-positive microorganisms.

17 Claims, 5 Drawing Sheets

OTHER PUBLICATIONS

Nishiyama, et al., "A novel membrane protein involved in protein translocation across the cytoplasmic membrane of *Escherichia coli*," *The EMBO Journal,* vol. 12, No. 9, pp. 3409–3415, 1993.

Nishiyama et al., "Disruption of the gene encoding p12 (SecG) reveals the direct involvement and important function of SecG in the protein translocation of *Escherichia coli* at low temperature," *The EMBO Journal,* vol. 13, No. 14, pp. 3272–3277, 1994.

Palva, Ilkka, "Molecular cloning of α–amylase gene from *Bacillus amyloliquefaciens* and its expression in *B. Subtilis,*" *Gene,* vol. 19, pp. 81–87, 1982.

Porath, Jerker "Immobilized Metal Ion Affinity Chromatography," *Protein Expression and Purification,* vol. 3, pp. 263–281, 1992.

Sambrook, J. et al., Molecular Cloning, A Laboratory Manual, $2^{nd}$ ed. Cold Spring Harbor Laboratory Press, Ch. 1–4, 1989.

Smith, Michael et al., "Protoplast Transformation in Coryneform Bacteria and Introduction of an α–Amylase Gene from *Bacillus amyloliquefaciens* into *Brevibacterium lactofermentum,*" *Applied and Environmental Microbiology,* vol. 51, No. 3, pp. 634–639, Mar., 1986.

Suh, J.W. et al., "Isolation of a secYhomologue from *Bacillus subtilis*: evidence for a common protein export pathway in eubacteria," *Molecular Microbiology,* vol. 4, No. 2, pp. 305–314, 1990.

van der Does, Chris et al., "Interaction between SecA and SecYEG in Micellar Solution and Formation of the Membrane–Inserted State," *Biochemistry* vol. 37, pp. 201–210, 1998.

van der Does, Chris et al., "SecA is an intrinsic subunit of the *Escherichia coli* preprotein translocase and exposes its carboxyl terminus to the periplasm," *Molecular Microbiolgy,* vol. 22, No. 4, pp. 619–629, 1996.

van der Vossen, Jos. et al., "Isolation and Characterization of *Streptococcus cremoris* Wg2–Specific Promoters," Applied and Environmental Microbiology, vol. 53, No. 10, pp. 2452–2457, Oct., 1987.

van der Wolk, J. et al., "Characterization of a *Bacillus subtilis* SecA mutant protein deficient ATPase and release from the membrane," Molecular Microbiology, vol. 8, No. 1, pp. 31–42, 1993.

Van Wely, K. et al., "Translocation of the precursor of α–amylase into *Bacillus subtilis* membrane vesicles," *Eur. J. Biochem.,* vol. 255, pp. 690–697, 1998.

Vorobjeva, I.P. et al., "Transformation of *Bacillus Megaterium* Protoplasts by Plasmid DNA," *FEMS Microbiology Letters* 7, pp. 261–263, 1980.

Weinrauch et al., "Plasmid Marker Rescue Transformation Proceeds by Breakage–Reunion in *Bacillus subtilis ,*" *Journal of Bacteriology,* vol. 169, No. 3, pp. 1205–1211, Mar., 1987.

Weinrauch et al., "Plasmid Marker Rescue Transformation in *Bacillus subtilis,*" *Journal of Bacteriology,* vol. 154, No. 3, pp. 1077–1087, Jun., 1983.

Yang, Maria et al., "Cloning of the Neutral Protease Gene of *Bacillus subtilis* an the Use of the Cloned Gene to Create and In Vitro–Derived Deletion Mutation," *Journal of Bacteriology,* vol. 160, No. 1, pp. 15–21, 1984.

PCT International Search Report .

* cited by examiner

FIG._1

```
            10                      30
atgcacgcagtttgattacttattggttatcgtcagcattgcactt
 M  H  A  V  L  I  T  L  L  V  I  V  S  I  A  L
   50                      70                      90
attattgtctttgcttcaatccagtaaagtgccggattatctggt
 I  I  V  L  Q  S  K  S  A  G  L  S  G
                110                     130
gcgatttcaggcgggagcggagcagctcttcgggaaacaaaagcaaga
 A  I  S  G  G  A  E  Q  L  F  G  K  Q  K  A  R
       150                     170                     190
ggtctttgatttaatttgcaccgcattacggtagtgctggcagtcttg
 G  L  D  L  I  L  H  R  I  T  V  V  L  A  V  L
                210
tttttcgtgttaacgattgcgcttgcttatatccta
 F  F  V  L  T  I  A  L  A  Y  I  L
```

FIG._2

```
              1   MYEALLVVFL IVAIGLVGLI MLQQGKGADM GASFGAGASA TLFGSSGSGN
ecosecg.pl        MYEALLVVFL IVAIGLVGLI MLQQGKGADM GASFGAGASA TLFGSSGSGN
haeinsecg.pl      MYQVLLFIYV VVAIALIGFI LVQQGKGANA GASFGGGASG TMFGSAGAGN
myclepsecg.pl     MELALQITLV VTSILVLLV  LLHRAKGGGL STLFGGGVQS SLSGSTVVEK
bsuyval.pl        MHAVLITLLV IVSIALIVV  LLQSSKSAGL SGAISGGAEQ LFGKQKARGL
Consensus         MY--LL---LV -V-IAL-GL- LLQQGKGAGL -ASFGGGAS- TLFGS-G-GN 100
              51  FMTRMTALLA TLFFIISLVL GNINSNKTNK GSEWENLSAP AKTEQTQPAA
ecosecg.pl        FMTRMTALLA TLFFIISLVL GNINSNKTNK GSEWENLSAP AKTEQTQPAA
haeinsecg.pl      FLTRTSAILA TAFFVIALVL GNMNSHKGNV QKGTFDDLSQ AAEQVQQQAA
myclepsecg.pl     NLDRLTLFVT GIWLVSIIGV ALLTKYR---
bsuyval.pl        DLILHRITVV LAVLFFVLTI ALAYIL----
Consensus         FLTR-TA--A TAF-VI-LVL ---NS-K-N- ------------ A------Q-AA 101 PAKPTSDIPN  112
ecosecg.pl        PAKPTSDIPN  ~~
haeinsecg.pl      PAKDNKNSDI PQ
myclepsecg.pl     ~~~~~~~~~~  ~~
bsuyval.pl        ~~~~~~~~~~  ~~
Consensus         PAK-------  --
```

```
             1                                                    50
ecosecg.p1   MYEALLVVFL IVAIGLVGLI MLQQGKGADM GASFGAGASA TLFGSSGSGN
bsuyval.p1   MHAVLITLLV IVSIALIIVV LLQSSKSAGL SGAISGGAEQ -LFGKQKA-R
Consensus    M--*L-*-*  IV-I*L-**  -LQ--K-A-- -*---*GA-- -LFG------

51                                                  100
ecosecg.p1   FMT----RMT ALLATLFFII SLVLGNINSNKTNK GSEWENLSAP AKTEQTQPAA
bsuyval.p1   GLDLILHRIT VVLAVLFFVL TIALAYIL--- ---------- ----------
Consensus    ------R-T  LA-LFF  ***L-*-I--- ---------- ----------

101        110
ecosecg.p1   PAKPTSDIPN
bsuyval.p1   ----------
Consensus    ----------
```

FIG._3

```
                          10         20         30         40         50         60
myclepsecg.p   MELALQITLVVTSILVVLLVLLHRAKGGGLSTLFGGGVQSSLSGSTV--VEKNLDRLTLF
                |::| |::: |||:|||| :::||| || :: ::  | |:::| |
bsuyval        MHAVLITLLVIVSIALIIVVLLQSSKSAGLSGAISGGAEQLFGKQKARGLDLILHRITVV 60         70
myclepsecg.p   VTGIWLVSIIGVALLTKYR
               :: :::| |: :| |
bsuyval        LAVLFFVLTIALAYIL
                          70
```

FIG._4

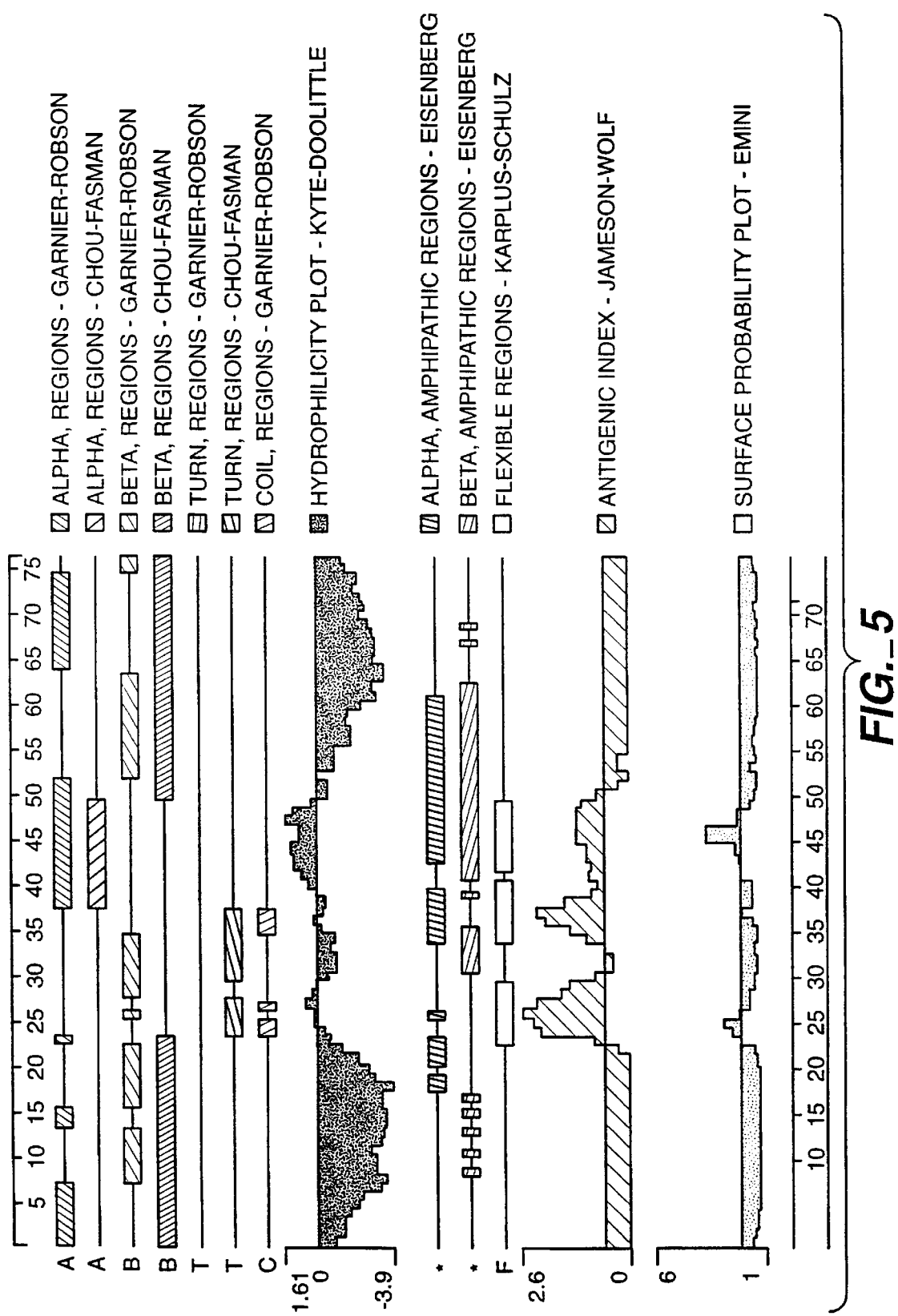
FIG._5

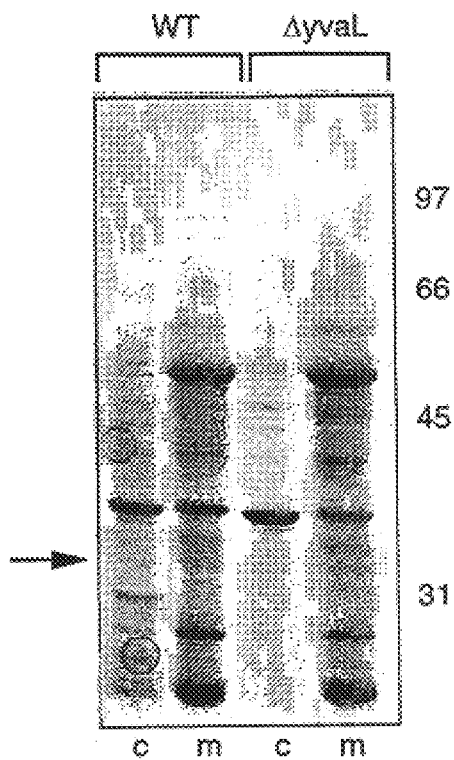
FIG._6A
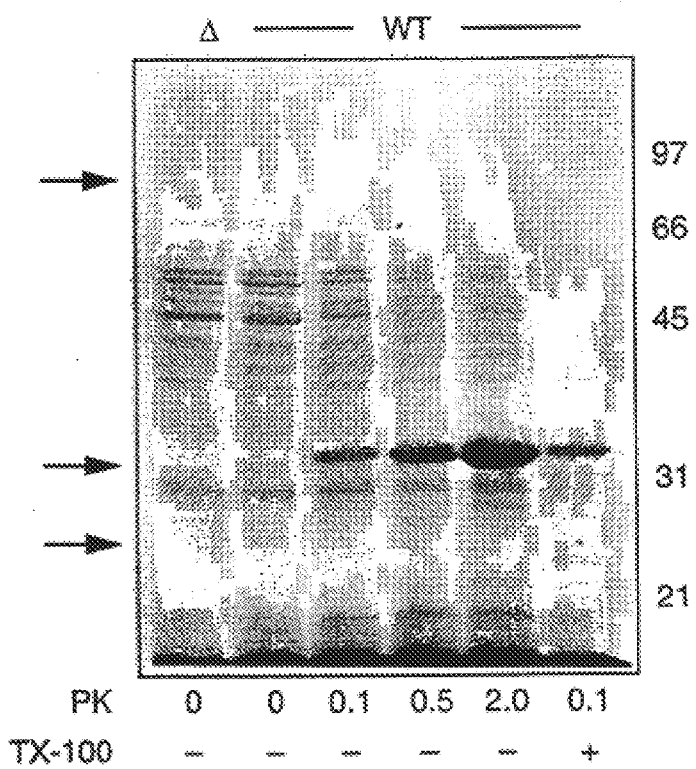
FIG._6B

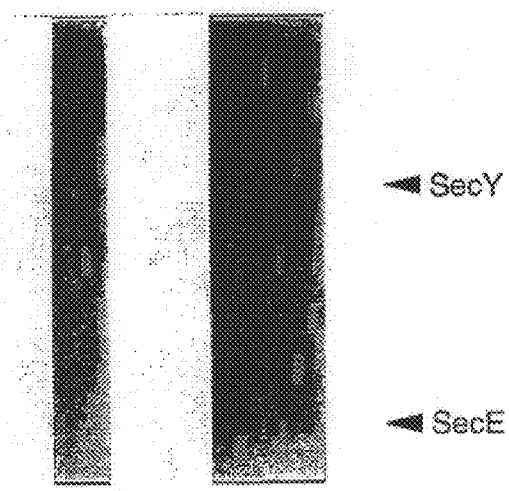
FIG._7A ◄ SecY
◄ SecE
FIG._7B ◄ SecG
FIG._7C ◄ YvaL
| Bs SecYE | − | + | + |
| Ec SecG | − | + | − |
| Bs YvaL | − | − | + |
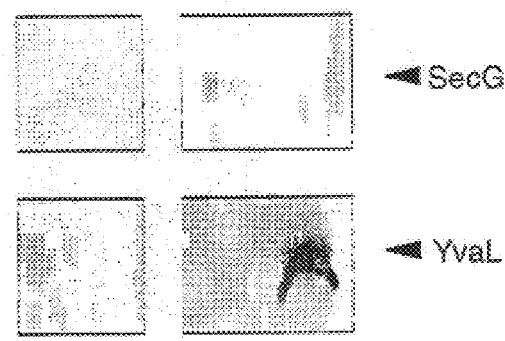
Bs SecA
FIG._8
◄ prePhoB
◄ PhoB
◄ prePhoB
◄ PhoB
| Bs SecYE | − | + | + |
| Ec SecG | − | + | − |
| Bs YvaL | − | − | + |

_US 6,506,579 B1_

SEQUENCE LISTING

```
<160> NUMBER OF SEQ ID NOS: 19

<210> SEQ ID NO 1
<211> LENGTH: 228
<212> TYPE: DNA
<213> ORGANISM: Bacillus subtilis
```

-continued

```
<400> SEQUENCE: 1
atgcacgcag ttttgattac cttattggtt atcgtcagca ttgcacttat tattgtcgtt      60
ttgcttcaat ccagtaaaag tgccggatta tctggtgcga tttcaggcgg agcggagcag     120
ctcttcggga aacaaaaagc aagaggtctt gatttaattt tgcaccgcat tacggtagtg     180
ctggcagtct tgttttcgt gttaacgatt gcgcttgctt atatccta                    228

<210> SEQ ID NO 2
<211> LENGTH: 76
<212> TYPE: PRT
<213> ORGANISM: Bacillus subtilis

<400> SEQUENCE: 2

Met His Ala Val Leu Ile Thr Leu Leu Val Ile Val Ser Ile Ala Leu
 1               5                  10                  15

Ile Ile Val Val Leu Leu Gln Ser Ser Lys Ser Ala Gly Leu Ser Gly
            20                  25                  30

Ala Ile Ser Gly Gly Ala Glu Gln Leu Phe Gly Lys Gln Lys Ala Arg
        35                  40                  45

Gly Leu Asp Leu Ile Leu His Arg Ile Thr Val Val Leu Ala Val Leu
    50                  55                  60

Phe Phe Val Leu Thr Ile Ala Leu Ala Tyr Ile Leu
65                  70                  75

<210> SEQ ID NO 3
<211> LENGTH: 110
<212> TYPE: PRT
<213> ORGANISM: Escherichia coli

<400> SEQUENCE: 3

Met Tyr Glu Ala Leu Leu Val Val Phe Leu Ile Val Ala Ile Gly Leu
 1               5                  10                  15

Val Gly Leu Ile Met Leu Gln Gln Gly Lys Gly Ala Asp Met Gly Ala
            20                  25                  30

Ser Phe Gly Ala Gly Ala Ser Ala Thr Leu Phe Gly Ser Ser Gly Ser
        35                  40                  45

Gly Asn Phe Met Thr Arg Met Thr Ala Leu Leu Ala Thr Leu Phe Phe
    50                  55                  60

Ile Ile Ser Leu Val Leu Gly Asn Ile Asn Ser Asn Lys Thr Asn Lys
65                  70                  75                  80

Gly Ser Glu Trp Glu Asn Leu Ser Ala Pro Ala Lys Thr Glu Gln Thr
                85                  90                  95

Gln Pro Ala Ala Pro Ala Lys Pro Thr Ser Asp Ile Pro Asn
            100                 105                 110

<210> SEQ ID NO 4
<211> LENGTH: 112
<212> TYPE: PRT
<213> ORGANISM: Haemophilus influenza

<400> SEQUENCE: 4

Met Tyr Gln Val Leu Leu Phe Ile Tyr Val Val Ala Ile Ala Leu
 1               5                  10                  15

Ile Gly Phe Ile Leu Val Gln Gln Gly Lys Gly Ala Asn Ala Gly Ala
            20                  25                  30

Ser Phe Gly Gly Gly Ala Ser Gly Thr Met Phe Gly Ser Ala Gly Ala
        35                  40                  45
```

```
Gly Asn Phe Leu Thr Arg Thr Ser Ala Ile Leu Ala Thr Ala Phe Phe
     50                  55                  60

Val Ile Ala Leu Val Leu Gly Asn Met Asn Ser His Lys Gly Asn Val
 65                  70                  75                  80

Gln Lys Gly Thr Phe Asp Asp Leu Ser Gln Ala Ala Glu Gln Val Gln
                 85                  90                  95

Gln Gln Ala Ala Pro Ala Lys Asn Lys Asn Ser Asp Ile Pro Gln
                100                 105                 110

<210> SEQ ID NO 5
<211> LENGTH: 77
<212> TYPE: PRT
<213> ORGANISM: Mycoplasma

<400> SEQUENCE: 5

Met Glu Leu Ala Leu Gln Ile Thr Leu Val Val Thr Ser Ile Leu Val
  1               5                  10                  15

Val Leu Val Leu Leu His Arg Ala Lys Gly Gly Leu Ser Thr
                 20                  25                  30

Leu Phe Gly Gly Gly Val Gln Ser Ser Leu Ser Gly Ser Thr Val Val
             35                  40                  45

Glu Lys Asn Leu Asp Arg Leu Thr Leu Phe Val Thr Gly Ile Trp Leu
     50                  55                  60

Val Ser Ile Ile Gly Val Ala Leu Leu Thr Lys Tyr Arg
 65                  70                  75

<210> SEQ ID NO 6
<211> LENGTH: 112
<212> TYPE: PRT
<213> ORGANISM: Artificial Sequence
<220> FEATURE:
<221> NAME/KEY: VARIANT
<222> LOCATION: (1)...(112)
<223> OTHER INFORMATION: Xaa = Any Amino Acid
<220> FEATURE:
<223> OTHER INFORMATION: consensus sequence

<400> SEQUENCE: 6

Met Tyr Xaa Xaa Leu Leu Xaa Xaa Leu Val Xaa Val Xaa Ile Ala Leu
  1               5                  10                  15

Xaa Gly Leu Xaa Leu Leu Gln Gln Gly Lys Gly Ala Gly Leu Xaa Ala
                 20                  25                  30

Ser Phe Gly Gly Gly Ala Ser Xaa Thr Leu Phe Gly Ser Xaa Gly Xaa
             35                  40                  45

Gly Asn Phe Leu Thr Arg Xaa Thr Ala Xaa Xaa Ala Thr Ala Phe Xaa
     50                  55                  60

Val Ile Xaa Leu Val Leu Xaa Xaa Xaa Asn Ser Xaa Lys Xaa Asn Xaa
 65                  70                  75                  80

Xaa Xaa Xaa Xaa Xaa Xaa Xaa Xaa Xaa Ala Xaa Xaa Xaa Xaa Xaa Xaa
                 85                  90                  95

Gln Xaa Ala Ala Pro Ala Lys Xaa Xaa Xaa Xaa Xaa Xaa Xaa Xaa
                100                 105                 110

<210> SEQ ID NO 7
<211> LENGTH: 110
<212> TYPE: PRT
<213> ORGANISM: Artificial Sequence
<220> FEATURE:
<221> NAME/KEY: VARIANT
<222> LOCATION: (1)...(110)
<223> OTHER INFORMATION: Xaa = Any Amino Acid
```

<220> FEATURE:
<223> OTHER INFORMATION: consensus sequence

<400> SEQUENCE: 7

Met Xaa Xaa Xaa Leu Xaa Xaa Xaa Xaa Ile Val Xaa Ile Xaa Leu
 1               5                  10                  15

Xaa Xaa Xaa Xaa Xaa Leu Gln Xaa Xaa Lys Xaa Ala Xaa Xaa Xaa
             20                  25                  30

Xaa Xaa Xaa Xaa Gly Ala Xaa Xaa Xaa Leu Phe Gly Xaa Xaa Xaa
         35                  40                  45

Xaa Xaa Xaa Xaa Xaa Xaa Xaa Xaa Arg Xaa Thr Xaa Xaa Leu Ala
         50                  55                  60

Xaa Leu Phe Phe Xaa Xaa Xaa Xaa Xaa Leu Xaa Xaa Ile Xaa Xaa Xaa
 65                  70                  75                  80

Xaa Xaa Xaa Xaa Xaa Xaa Xaa Xaa Xaa Xaa Xaa Xaa Xaa Xaa Xaa
             85                  90                  95

Xaa Xaa Xaa Xaa Xaa Xaa Xaa Xaa Xaa Xaa Xaa Xaa Xaa
         100                 105                 110

<210> SEQ ID NO 8
<211> LENGTH: 30
<212> TYPE: PRT
<213> ORGANISM: Artificial Sequence
<220> FEATURE:
<221> NAME/KEY: VARIANT
<222> LOCATION: (1)...(30)
<223> OTHER INFORMATION: Xaa = Any Amino Acid
<220> FEATURE:
<223> OTHER INFORMATION: consensus sequence

<400> SEQUENCE: 8

Leu Val Gly Leu Ile Leu Leu Gln Gln Gly Lys Gly Ala Xaa Xaa Gly
 1               5                  10                  15

Ala Ser Phe Gly Gly Gly Ala Ser Xaa Thr Leu Phe Gly Ser
             20                  25                  30

<210> SEQ ID NO 9
<211> LENGTH: 35
<212> TYPE: DNA
<213> ORGANISM: Artificial Sequence
<220> FEATURE:
<223> OTHER INFORMATION: primer

<400> SEQUENCE: 9
cgcccatggt taaaaacaat ctccaacttt atgcg                     35

<210> SEQ ID NO 10
<211> LENGTH: 33
<212> TYPE: DNA
<213> ORGANISM: Artificial Sequence
<220> FEATURE:
<223> OTHER INFORMATION: primer

<400> SEQUENCE: 10
cgcgtcgact tagtttttca taaatccacg gta                       33

<210> SEQ ID NO 11
<211> LENGTH: 38
<212> TYPE: DNA
<213> ORGANISM: Artificial Sequence
<220> FEATURE:
<223> OTHER INFORMATION: primer

<400> SEQUENCE: 11
gggatcgatg gaggtttaa ttcatgcgta ttatgaaa                                    38

<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12
cgcggatcct cattattcaa ctattaa                                              27

<210> SEQ ID NO 13
<211> LENGTH: 32
<212> TYPE: DNA
<213> ORGANISM: Artificial Sequence
<220> FEATURE:
<223> OTHER INFORMATION: primer

<400> SEQUENCE: 13
aaaggatcct agtctggagg tgtatgggat gc                                        32

<210> SEQ ID NO 14
<211> LENGTH: 38
<212> TYPE: DNA
<213> ORGANISM: Artificial Sequence
<220> FEATURE:
<223> OTHER INFORMATION: primer

<400> SEQUENCE: 14
aaatctagat tctcgagccc tataggatat aagcaagc                                  38

<210> SEQ ID NO 15
<211> LENGTH: 39
<212> TYPE: DNA
<213> ORGANISM: Artificial Sequence
<220> FEATURE:
<223> OTHER INFORMATION: primer

<400> SEQUENCE: 15
cccggatccg gaggtttaa ttcatgtatg aagctcttt                                  39

<210> SEQ ID NO 16
<211> LENGTH: 32
<212> TYPE: DNA
<213> ORGANISM: Artificial Sequence
<220> FEATURE:
<223> OTHER INFORMATION: primer

<400> SEQUENCE: 16
ccctctagac tcgagttagt tcgggatatc gc                                        32

<210> SEQ ID NO 17
<211> LENGTH: 29
<212> TYPE: DNA
<213> ORGANISM: Artificial Sequence
<220> FEATURE:
<223> OTHER INFORMATION: primer

<400> SEQUENCE: 17
gggccatggg aaaaaaattc ccaaagaaa                                            29

<210> SEQ ID NO 18
<211> LENGTH: 30
<212> TYPE: DNA

-continued

```
<213> ORGANISM: Artificial Sequence
<220> FEATURE:
<223> OTHER INFORMATION: primer

<400> SEQUENCE: 18
gggggatcct tacttatcgt taatcttaat                              30

<210> SEQ ID NO 19
<211> LENGTH: 15
<212> TYPE: PRT
<213> ORGANISM: Artificial Sequence
<220> FEATURE:
<223> OTHER INFORMATION: internal YvaL sequence

<400> SEQUENCE: 19

Tyr Ala Glu Gln Leu Phe Gly Lys Gln Lys Ala Arg Gly Leu Asp
1               5                   10                  15
```

INCREASING PRODUCTION OF PROTEINS IN GRAM-POSITIVE MICROORGANISMS USING SECG

FIELD OF THE INVENTION

The present invention generally relates to expression of proteins in gram-positive microorganisms and specifically to the gram positive microorganism secretion factor, SecG. The present invention also provides expression vectors, methods and systems for the production of proteins in gram-positive microorganisms.

BACKGROUND OF THE INVENTION

Gram-positive microorganisms, such as members of the group Bacillus, have been used for large-scale industrial fermentation due, in part, to their ability to secrete their fermentation products into the culture media. In gram-positive bacteria, secreted proteins are exported across a cell membrane and a cell wall, and then are subsequently released into the external media usually obtaining their native conformation.

Secretion factors from Gram-positive microorganisms which have been identified and reported in the literature include SecA (Sadaie Y., Takamatsu h., Nakamura k., Yamane k.; Gene 98:101–105, 1991)., SecY (Suh J.-W., Boylan S. A., Thomas S. M., Dolan K. M., Oliver D. B., Price C. W.; Mol. Microbiol. 4:305–314, 1990)., SecE (Jeong S., Yoshikawa H., Takahashi H.; Mol. Microbiol. 10:133–142, 1993), FtsY an FfH (PCT/NL 96/00278), and PrsA (WO 94/19471).

By contrast, in the gram-negative microorganism, _E.coli_, protein is transported to the periplasm rather than across the cell membrane and cell wall and into the culture media. _E.coli_ has at least two types of components of the secretory mechanism, soluble cytoplasmic proteins and membrane associated proteins. Reported _E.coli_ secretion factors include the soluble cytoplasmic proteins, SecB and heat shock proteins; the peripheral membrane-associated protein SecA; and the integral membrane proteins SecY, SecE, SecD and SecF.

In spite of advances in understanding portions of the protein secretion machinery in procaryotic cells, the complete mechanism of protein secretion, especially for gram-positive microorganisms, such as Bacillus, has yet to be fully elucidated.

SUMMARY OF THE INVENTION

The capacity of the secretion machinery of a Gram-positive microorganism may become a limiting factor or bottleneck to protein secretion and the production of proteins in secreted form, in particular when the proteins are recombinantly introduced and overexpressed by the host cell. The present invention provides a means for alleviating that bottle neck.

The present invention is based, in part, upon the discovery of a _Bacillus subtilis_ SecG secretion factor (also referred to herein as YVAL) identified in heretofore uncharacterised translated genomic DNA by its homology with a consensus sequence for SecG (based upon SecG sequences for Escherichia, Haemophilus, and Mycoplasma organisms) and the demonstration that _B. subtilis_ SecG is a functional homolog of _E.coli_ Sec G. The present invention is also based, in part, upon the discovery that _B.subtilis_ SecG in combination with other _B.subtilis_ secretion factors forms a functional preprotein translocase.

The present invention provides isolated nucleic acid and deduced amino acid sequences for _B. subtilis_ SecG. The amino acid sequence for _B. subtilis_ SecG is shown in FIG. 1 (SEQ ID No:1). The nucleic acid sequence encoding _B. subtilis_ SecG is shown in FIG. 1 (SEQ ID No:2).

The present invention also provides improved methods for secreting proteins from gram-positive microorganisms. Accordingly, the present invention provides an improved method for secreting a desired protein in a gram-positive microorganism comprising the steps of obtaining a gram-positive microorganism host cell comprising nucleic acid encoding SecG wherein said nucleic acid is under the control of expression signals capable of expressing SecG in a gram-positive microorganism said microorganism further comprising nucleic acid encoding said protein; and culturing said microorganism under conditions suitable for expression of SecG and expression and secretion of said protein. in one embodiment of the present invention, the desired protein is homologous or naturally occurring in the gram-positive microorganism. In another embodiment of the present invention, the desired protein is heterologous to the gram-positive microorganism.

In one aspect of the present invention, a microorganism is genetically engineered to produce a desired protein, such as an enzyme, growth factor or hormone. The enzyme is selected from the group consisting of proteases, carbohydrases including amylases, cellulases, xylanases, and lipases; isomerases such as racemases, epimerases, tautomerases, or mutases; transferases, kinases and phophatases acylases, amidases, esterases, reductases, oxidases. In a further embodiment the expression of the secretion factor SecG is coordinated with the expression of other components of the secretion machinery. Preferably other components of the secretion machinary, i.e., translocase, SecA, SecY, SecE and/or other secretion known to those of skill in the art are modulated in expression at an optimal ratio to SecG. For example, it may be desired to overexpress multiple secretion factors in addition to SecG for optimum enhancement of the secretion machinary. In one particular embodiment disclosed herein, _B.subtilis_ SecG is expressed along with _B.subtilis_ SecYE and SecA to form a functional preprotein translocase.

The present invention also provides a method of identifying homologous gram positive microorganism SecG that comprises hybridizing part or all of _B. subtilis_ SecG nucleic acid shown in FIG. 1 (SEQ ID No:1) with nucleic acid derived from gram-positive microorganisms. In one embodiment, the nucleic acid is of genomic origin. In another embodiment, the nucleic acid is a cDNA. The present invention encompasses novel gram-positive microorganism secretion factors identified by this method.

BRIEF DESCRIPTION OF THE DRAWINGS

FIG. 1 shows the nucleic acid sequence for secG (SEQ ID No:1) and the amino acid sequence of SecG (SEQ ID No:2).

FIG. 2 shows the SecG sequence from _E. coli_ (ecosecg.p1) (SEQ ID No:3), Haemophilus (haeinsecg.p1) (SEQ ID No:4), Mycoplasma (myclepsecg.p1) (SEQ ID No:5) and _B.subtilis_ (bsuyval.p1) (SEQ ID No:2) and the SecG consensus sequence (SEQ ID No:6) of the four organisms.

FIG. 3 shows the amino acid identity (SEQ ID No:7) between _B.subtilis_ SecG (SEQ ID No:2) and _E.coli_ SecG (SEQ ID No:3).

FIG. 4 shows the amino acid identity between _B.subtilis_ SecG (SEQ ID No:2) and Mycoplasma SecG (SEQ ID No:5).

FIG. 5 shows a hydrophilicity profile of *B.subtilis* SecG.

FIGS. 6A–6B. FIG. 6A shows a commassie stained SDS-PAGE of cell fractions of *B.subtilis* DB104 and DB104:ΔyvaL. Lower case "c" refers to cellular fraction; lower case "m" refers to medium. The position of a polypeptide band is indicated that is present in the wild-type cells but absent in the deletion mutant. FIG. 6B shows the proteinase K digestion of cell associated proteins. The digestion of the polypeptide band at 30 kDa is absent in the DB104: ΔyvaL cells. The final lane shows a control with triton X-100 to demonstrate that proteinase K is present in excess amounts.

FIGS. 7A–7C.

FIG. 7A shows a commassie stained SDS-PAGE of *E.coli* inner membrane vesicles expressing the *B.subtilis* SecYE and either *E.coli* SecG or *B.subtilis* SecG (YvaL) compared to wild type vesicles. The position of *B.subtilis* SecY and SecE is indicated.

FIG. 7B shows an immunoblot developed with a pAb directed against a synthetic polypeptide of *E.coli* SecG.

FIG. 7C shows an immunoblot developed with a pAb directed against a synthetic polypeptide of *B.subtilis* SecG.

FIG. 8 shows an In vitro translocation of $^{125}$I-labelled prePhoB into *E.coli* inside out vesicles. Vesicles were stripped for SecA and purified *B.subtilis* SecA was added when indicated.

DETAILED DESCRIPTION

Definitions

As used herein, the genus Bacillus includes all members known to those of skill in the art, including but not limited to *B. subtilis, B. licheniformis, B. lentus, B. brevis, B. stearothermophilus, B. alkalophilus, B. amyloliquefaciens, B. coagulans, B. circulans, B. lautus* and *B. thuringiensis.*

The present invention encompasses novel SecG secretion factors from gram positive microorganism. In a preferred embodiment, the gram-positive organism is Bacillus. In another preferred embodiment, the gram-positive organism is *B. subtilis*. As used herein, the phrase, "*B.subtilis* SecG secretion factor" refers to the deduced amino acid sequence shown in FIG. 1 (SEQ ID No:2). The present invention encompasses variants of the amino acid sequence disclosed in FIG. 1 that are able to modulate secretion alone or in combination with other secretions factors.

As used herein, "nucleic acid" refers to a nucleotide or polynucleotide sequence, and fragments or portions thereof, and to DNA or RNA of genomic or synthetic origin which may be double-stranded or single-stranded, whether representing the sense or antisense strand. As used herein "amino acid" refers to peptide or protein sequences or portions thereof. As used herein, lower case "secG" is used to designate a nucleic acid sequence, whereas upper case "SecG" is used to designate an amino acid sequence. A "*B.subtilis* polynucleotide homolog" or "polynucleotide homolog" as used herein refers to a novel polynucleotide that has at least 80%, at least 90% and at least 95% identity to the secG polynucleotide in FIG. 1 (SEQ ID No:1) or which is capable of hybridizing to the polynucleotide of FIG. 1 (SEQ ID No:2) under conditions of high stringency and which encodes an amino acid sequence that is able to modulate secretion of the gram-positive microorganism from which it is derived. Modulate as used herein refers to the ability of a secretion factor to alter the secretion patterns of proteins.

The terms "isolated" or "purified" as used herein refer to a nucleic acid or amino acid that is removed from at least one component with which it is naturally associated.

As used herein, the term "heterologous protein" refers to a protein or polypeptide that does not naturally occur in a gram-positive host cell. Examples of heterologous proteins include enzymes such as hydrolases including proteases, cellulases, amylases, other carbohydrases, and lipases; isomerases such as racemases, epimerases, tautomerases, or mutases; transferases, kinases and phophatases. The heterologous gene may encode therapeutically significant proteins or peptides, such as growth factors, cytokines, ligands, receptors and inhibitors, as well as vaccines and antibodies. The gene may encode commercially important industrial proteins or peptides, such as proteases, carbohydrases such as amylases and glucoamylases, cellulases, oxidases and lipases. The gene of interest may be a naturally occurring gene, a mutated gene or a synthetic gene.

The term "homologous protein" refers to a protein or polypeptide native or naturally occurring in a gram-positive host cell. The invention includes host cells producing the homologous protein via recombinant DNA technology. The present invention encompasses a gram-positive host cell having a deletion or interruption of the nucleic acid encoding the naturally occurring homologous protein, such as a protease, and having nucleic acid encoding the homologous protein, or a variant thereof re-introduced in a recombinant form. In another embodiment, the host cell produces the homologous protein.

DETAILED DESCRIPTION OF THE PREFERRED EMBODIMENTS

The present invention provides novel gram-positive microorganism secretion factors and methods that can be used in gram-positive microorganisms to ameliorate the bottleneck to protein secretion and the production of proteins in secreted form, in particular when the proteins are recombinantly introduced and overexpressed by the host cell. The present invention provides the secretion factor SecG derived from *Bacillus subtilis*.

I. SecG Nucleic Acid and Amino Acid Sequences
SecG Nucleic Acid Sequences

The SecG polynucleotide having the sequence as shown in FIG. 1 (SEQ ID No:1) encodes the *Bacillus subtilis* secretion factor SecG. A FASTA search of *Bacillus subtilis* translated genomic sequences with the *E.coli* SecG sequence alone did not identify the *B. subtilis* SecG. The *Bacillus subtilis* SecG was identified via a FASTA search of *Bacillus subtilis* translated genomic sequences using a consensus sequence of 30 amino acids of SecG derived from *E.coli*, Haemophilus (SEQ ID No:4) and Mycoplasma species (SEQ ID No:5) as shown in FIG. 2. The consensus sequence used was "LVGLILLQQG KGAXXGASFG GGASX-TLFGS" (SEQ ID No:8) given in the amino terminus to carboxy terminus direction with the FASTA search (Release 1.0, released on Jun. 11, 1997) parameters being Scoring matrix: GenRunData: blosum50.cmp; variable pamfactor used; Gap creation penalty: 12; and Gap extension penalty: 2.

The present invention provides gram-positive secG polynucleotides which may be used alone or together with other secretion factors, such as SecY, SecE and SecA, in a gram-positive host cell for the purpose of increasing the secretion of desired heterologous or homologous proteins or polypeptides.

The present invention encompasses secG polynucleotide homologs encoding novel gram-positive microorganism SecG whether encoded by one or multiple polynucleotides which have at least 80%, or at least 90% or at least 95% identity to *B. subtilis* SecG as long as the homolog encodes a protein that is able to function by modulating secretion in a gram-positive microorganism. As will be understood by the skilled artisan, due to the degeneracy of the genetic code, a variety of polynucleotides, i.e., SecG polynucleotide variants, can encode the *Bacillus subtilis* secretion factors SecG. The present invention encompasses all such polynucleotides.

Gram-positive polynucleotide homologs of *B.subtilis* SecG may be obtained by standard procedures known in the art from, for example, cloned DNA (e.g., a DNA "library"), genomic DNA libraries, by chemical synthesis once identified, by cDNA cloning, or by the cloning of genomic DNA, or fragments thereof, purified from a desired cell. (See, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U.K. Vol. I, II.) A preferred source is from genomic DNA. Nucleic acid sequences derived from genomic DNA may contain regulatory regions in addition to coding regions. Whatever the source, the isolated secG gene should be molecularly cloned into a suitable vector for propagation of the gene.

In the molecular cloning of the gene from genomic DNA, DNA fragments are generated, some of which will encode the desired gene. The DNA may be cleaved at specific sites using various restriction enzymes. Alternatively, one may use DNAse in the presence of manganese to fragment the DNA, or the DNA can be physically sheared, as for example, by sonication. The linear DNA fragments can then be separated according to size by standard techniques, including but not limited to, agarose and polyacrylamide gel electrophoresis and column chromatography.

Once the DNA fragments are generated, identification of the specific DNA fragment containing the SecG may be accomplished in a number of ways. For example, a *B.subtilis* SecG gene of the present invention or its specific RNA, or a fragment thereof, such as a probe or primer, may be isolated and labeled and then used in hybridization assays to detect a gram-positive SecG gene. (Benton, W. and Davis, R., 1977, *Science* 196:180; Grunstein, M. And Hogness, D., 1975, *Proc. Natl. Acad. Sci. USA* 72:3961). Those DNA fragments sharing substantial sequence similarity to the probe will hybridize under stringent conditions.

Accordingly, the present invention provides a method for the detection of gram-positive SecG polynucleotide homologs which comprises hybridizing part or all of a nucleic acid sequence of *B. subtilis* SecG with gram-positive microorganism nucleic acid of either genomic or cDNA origin.

Also included within the scope of the present invention are gram-positive microorganism polynucleotide sequences that are capable of hybridizing to the nucleotide sequence of *B.subtilis* SecG under conditions of intermediate to maximal stringency. Hybridization conditions are based on the melting temperature (Tm) of the nucleic acid binding complex, as taught in Berger and Kimmel (1987, *Guide to Molecular Cloning Techniques*, Methods in Enzymology, Vol 152. Academic Press, San Diego Calif.) incorporated herein by reference, and confer a defined "stringency" as explained below.

Also included within the scope of the present invention are novel gram-positive microorganism secG polynucleotide sequences that are capable of hybridizing to part or all of the secG nucleotide sequence of FIG. 1 under conditions of intermediate to maximal stringency. Hybridization conditions are based on the melting temperature (Tm) of the nucleic acid binding complex, as taught in Berger and Kimmel (1987, *Guide to Molecular Cloning Techniques*, Methods in Enzymology, Vol 152, Academic Press, San Diego Calif.) incorporated herein by reference, and confer a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate or low stringency hybridization can be used to identify or detect polynucleotide sequence homologs.

The term "hybridization" as used herein shall include "the process by which a strand of nucleic acid joins with a complementary strand through base pairing" (Coombs J (1994) *Dictionary of Biotechnology*, Stockton Press, New York N.Y.). The process of amplification as carried out in polymerase chain reaction (PCR) technologies is described in Dieffenbach CW and GS Dveksler (1995, *PCR Primer, a Laboratory Manual*, Cold Spring Harbor Press, Plainview N.Y.). A nucleic acid sequence of at least about 10 nucleotides and as many as about 60 nucleotides from the SecG nucleotide sequence of FIG. 1, preferably about 12 to 30 nucleotides, and more preferably about 20–25 nucleotides can be used as a probe or PCR primer.

Amino Acid Sequences

The *B. subtilis* secG polynucleotide as shown in FIG. 1 (SEQ ID No:1) encodes *B. subtilis* SecG (SEQ ID No:2). The present invention encompasses novel gram positive microorganism amino acid variants of the amino acid sequence shown in FIG. 1 (SEQ ID No:2) that are at least 80% identical, at least 90% identical and at least 95% identical to the sequence shown in FIG. 1 as long as the amino acid sequence variant is able to function by modulating secretion of proteins in gram-positive microorganisms alone or in combination with other secretion factors.

The secretion factor SecG as shown in FIG. 1 was subjected to a FASTA (Lipmann Pearson routine) amino acid search against a consensus amino acid sequence for SecG. The amino acid alignment is shown in FIG. 2. The hydrophilicity profile for *B.subtilis* SecG as shown in FIG. 5 shows two potential membrane spanning regions.

II. Expression Systems

The present invention provides expression systems for the enhanced production and secretion of desired heterologous or homologous proteins in gram-positive microorganisms.

a. Coding Sequences

In the present invention, the vector comprises at least one copy of nucleic acid encoding a gram-positive microorganism SecG secretion factor and preferably comprises multiple copies. In a preferred embodiment, the gram-positive microorganism is Bacillus. In another preferred embodiment, the gram-positive microorganism is *Bacillus subtilis*. In a preferred embodiment, polynucleotides which encode *B. subtilis* SecG, or fragments thereof, or fusion proteins or polynucleotide homolog sequences that encode amino acid variants of SecG, may be used to generate recombinant DNA molecules that direct the expression of SecG, or amino acid variants thereof, respectively, in gram-positive host cells. In a preferred embodiment, the host cell belongs to the genus Bacillus. In another preferred embodiment, the host cell is *B.subtilis*.

As will be understood by those of skill in the art, it may be advantageous to produce polynucleotide sequences possessing non-naturally occurring codons. Codons preferred by a particular gram-positive host cell (Murray E et al (1989) Nuc Acids Res 17:477–508) can be selected, for example, to increase the rate of expression or to produce recombinant RNA transcripts having desirable properties, such as a longer half-life, than transcripts produced from naturally occurring sequence.

Altered gram positive secG polynucleotide sequences which may be used in accordance with the invention include deletions, insertions or substitutions of different nucleotide residues resulting in a polynucleotide that encodes the same or a functionally equivalent secG homolog, respectively. As used herein a "deletion" is defined as a change in either nucleotide or amino acid sequence in which one or more nucleotides or amino acid residues, respectively, are absent.

As used herein an "insertion" or "addition" is that change in a nucleotide or amino acid sequence which has resulted in the addition of one or more nucleotides or amino acid residues, respectively, as compared to the naturally occurring gram positive secG.

As used herein "substitution" results from the replacement of one or more nucleotides or amino acids by different nucleotides or amino acids, respectively.

The encoded protein may also show deletions, insertions or substitutions of amino acid residues which produce a silent change and result in a functionally equivalent gram-positive secG variant. Deliberate amino acid substitutions may be made on the basis of similarity in polarity, charge, solubility, hydrophobicity, hydrophilicity, and/or the amphipathic nature of the residues as long as the variant retains the ability to modulate secretion. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine, phenylaianine, and tyrosine.

The secG polynucleotides of the present invention may be engineered in order to modify the cloning, processing and/or expression of the gene product. For example, mutations may be introduced using techniques which are well known in the art, eg, site-directed mutagenesis to insert new restriction sites, to alter glycosylation patterns or to change codon preference, for example.

In one embodiment of the present invention, a secG polynucleotide may be ligated to a heterologous sequence to encode a fusion protein. A fusion protein may also be engineered to contain a cleavage site located between the SecG nucleotide sequence and the heterologous protein sequence, so that the SecG protein may be cleaved and purified away from the heterologous moiety.

b. Vector Sequences

Expression vectors used in expressing the secretion factors of the present invention in gram-positive microorganisms comprise at least one promoter associated with a gram-positive SecG, which promoter is functional in the host cell. In one embodiment of the present invention, the promoter is the wild-type promoter for the selected secretion factor and in another embodiment of the present invention, the promoter is heterologous to the secretion factor, but still functional in the host cell.

Additional promoters associated with heterologous nucleic acid encoding desired proteins or polypeptides may be introduced via recombinant DNA techniques. In one embodiment of the present invention, the host cell is capable of overexpressing a heterologous protein or polypeptide and nucleic acid encoding one or more secretion factor(s) is(are) recombinantly introduced. In one preferred embodiment of the present invention, nucleic acid encoding SecG is stably integrated into the microorganism genome. In another embodiment, the host cell is engineered to overexpress a secretion factor of the present invention and nucleic acid encoding the heterologous protein or polypeptide is introduced via recombinant DNA techniques. Example III demonstrates that *B.subtilis* SecG can be overexpressed in a host cell. The present invention encompasses gram-positive host cells that are capable of overexpressing other secretion factors known to those of skill in the art, including but not limited to, SecA, SecY, SecE or other secretion factors known to those of skill in the art or identified in the future. In an embodiment disclosed herein in Example II, it is demonstrated that *B.subtilis* SecG along with *B.subtilis* secretion factors SecY, E, and A, is able to participate in forming a functional preprotein translocase.

In a preferred embodiment, the expression vector contains a multiple cloning site cassette which preferably comprises at least one restriction endonuclease site unique to the vector, to facilitate ease of nucleic acid manipulation. In a preferred embodiment, the vector also comprises one or more selectable markers. As used herein, the term selectable marker refers to a gene capable of expression in the gram-positive host which allows for ease of selection of those hosts containing the vector. Examples of such selectable markers include but are not limited to antibiotics, such as, erythromycin, actinomycin, chloramphenicol and tetracycline.

c. Transformation

In one embodiment of the present invention, nucleic acid encoding one or more gram-positive secretion factor(s) of the present invention is introduced into a gram-positive host cell via an expression vector capable of replicating within the host cell. Suitable replicating plasmids for Bacillus are described in Molecular Biological Methods for Bacillus, Ed. Harwood and Cutting, John Wiley & Sons, 1990, hereby expressly incorporated by reference; see chapter 3 on plasmids. Suitable replicating plasmids for *B. subtilis* are listed on page 92.

In another embodiment, nucleic acid encoding a gram-positive micro-organism SecG stably integrated into the microorganism genome. Preferred gram-positive host cells are from the genus Bacillus. Another preferred gram-positive host cell is *B. subtilis*. Several strategies have been described in the literature for the direct cloning of DNA in Bacillus. Plasmid marker rescue transformation involves the uptake of a donor plasmid by competent cells carrying a partially homologous resident plasmid (Contente et al., *Plasmid* 2:555–571 (1979); Haima et al., *Mop Gen. Genet.* 223:185–191 (1990); Weinrauch et al., *J. Bacteriol.* 154(3): 1077–1087 (1983); and Weinrauch et al., *J. Bacteriol.* 169 (3):1205–1211 (1987)). The incoming donor plasmid recombines with the homologous region of the resident "helper" plasmid in a process that mimics chromosomal transformation.

Transformation by protoplast transformation is described for *B. subtilis* in Chang and Cohen, (1979) Mol. Gen. Genet 168:111–115; for *B.megaterium* in Vorobjeva et al., (1980) FEMS Microbiol. Letters 7:261–263; for *B. amyloliquefaciens* in Smith et al., (1986) Appl. and Env. Microbiol. 51:634; for *B.thuringiensis* in Fisher et al., (1981) Arch. Microbiol. 139:213–217; for *B.sphaericus* in McDonald (1984) J. Gen. Microbiol. 130:203; and *B.larvae* in Bakhiet et al., (1985) 49:577. Mann et al., (1986, Current Microbiol.

13:131–135) report on transformation of Bacillus protoplasts and Holubova, (1985) Folia Microbiol. 30:97) disclose methods for introducing DNA into protoplasts using DNA containing liposomes.

III. Identification of Transformants

Although the presence/absence of marker gene expression suggests that the gene of interest is also present, its presence and expression should be confirmed. For example, if the nucleic acid encoding SecG is inserted within a marker gene sequence, recombinant cells containing the insert can be identified by the absence of marker gene function. Alternatively, a marker gene can be placed in tandem with nucleic acid encoding the secretion factor under the control of a single promoter. Expression of the marker gene in response to induction or selection usually indicates expression of the secretion factor as well.

Alternatively, host cells which contain the coding sequence for a secretion factor and express the protein may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

The presence of the secG polynucleotide sequence can be detected by DNA-DNA or DNA-RNA hybridization or amplification using probes, portions or fragments derived from the B.subtilis secG polynucleotide.

IV. Secretion Assays

In an embodiment disclosed herein in Example IV, it is demonstrated that a B.subtilis microorganism having a disruption in nucleic acid encoding SecG appears to be defective in the secretion of some extracellular proteins.

Means for determining the levels of secretion of a heterologous or homologous protein in a gram-positive host cell and detecting secreted proteins include, using either polyclonal or monoclonal antibodies specific for the protein. Examples include enzyme-linked immunosorbent assay (ELISA), radioimmunoassay (RIA) and fluorescent activated cell sorting (FACS). These and other assays are described, among other places, in Hampton R et al (1990, Serological Methods, a Laboratory Manual. APS Press, St Paul Minn.) and Maddox DE et al (1983, J Exp Med 158:1211).

A wide variety of labels and conjugation techniques are known by those skilled in the art and can be used in various nucleic and amino acid assays. Means for producing labeled hybridization or PCR probes for detecting specific polynucleotide sequences include oligolabeling, nick translation, end-labeling or PCR amplification using a labeled nucleotide. Alternatively, the nucleotide sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837: 3,850,752; 3,939,350; 3,996,345; 4,277,437; 4,275,149 and 4,366,241. Also, recombinant immunoglobulins may be produced as shown in U.S. Pat. No. 4,816,567 and incorporated herein by reference.

V. Purification of Proteins

Gram positive host cells transformed with polynucleotide sequences encoding heterologous or homologous protein may be cultured under conditions suitable for the expression and recovery of the encoded protein from cell culture. The protein produced by a recombinant gram-positive host cell comprising a secretion factor of the present invention will be secreted into the culture media. Other recombinant constructions may join the heterologous or homologous polynucleotide sequences to nucleotide sequence encoding a polypeptide domain which will facilitate purification of soluble proteins (Kroll DJ et al (1993) DNA Cell Biol 12:441–53).

Such purification facilitating domains include, but are not limited to, metal chelating peptides such as histidine-tryptophan modules that allow purification on immobilized metals (Porath J (1992) Protein Expr Purif 3:263–281), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and the heterologous protein can be used to facilitate purification.

The manner and method of carrying out the present invention may be more fully understood by those of skill in the art by reference to the following examples, which examples are not intended in any manner to limit the scope of the present invention or of the claims directed thereto. All publications and patents are hereby incorporated by reference in their entirety.

EXAMPLE I

Example I provides the Materials and Methods used in Examples II–VI.

a. Bacterial Strains and Growth Media

Strains were grown in Luria-Bertani Broth or on Luria-Bertani agar. When necessary, the medium was supplemented with relevant antibiotics as indicated. Construction of vectors was done in E. coli DH5α (supE44, ΔlacU169, (φ80lacZΔM15), hsdR17, recA1, endAI, gyrA96, thi-1, re1A1). Chromosomal deletions and growth experiments were done in B. subtilis DB104 (nprE18, aprEΔ3) (Yang et al., 1984, Journal of Bacteriology 160:15–21).

b. Construction of Plasmids

The E. coli secG and B. subtilis yvaL genes including suitable ribosome binding sites were amplified as BamHI-XbaI cassettes by PCR from chromosomal DNA from strains DH5α and DB104, respectively, and cloned into pBluescript SK+, the primer used are listed in Table 1. The sequences of both open reading frames were determined and compared against relevant databases. For expression in E. coli, the genes were cloned into pET324 (Van der Does et al., 1996) yielding pET304 (E. coli secG) and pET820 (B. subtilis yvaL).

Vectors pPR111 (a pUB110 derivative, Diderichsen et al., 1993, Plasmid 30:312–315) and pBEY13 (a gift from Dr. R. Breitlin) are shuttle vectors using a ColE1 origin for replication in E. coli and RepR for replication in gram-positive organisms. These plasmids encode ampicillin resistance markers for *E. coli* and phleomycin resistance markers for *B. subtilis*. Vector pBEY13 expresses the *B. subtilis* secY and secE genes from the constitutive staphylococcal sak promoter. Plasmids pET470 and pET471 were formed by replacing the secYE cassette by *E. coli* secG and *B. subtilis* yvaL respectively. Vector pAMP21 is a pGK13 (Kok et al., The alkaline phosphates phoB (phoAIII) of *B. subtilis* was amplified from chromosomal DNA of DB104 using PCR (for primers see Table 1) and N-terminally fused to a his-tag using the plasmid pET302 (van der Does et al., 1998, Biochemistry, 37: 201–210) so creating pET461. An overview of the plasmids used in this study is given in Table 2.

TABLE 1

PCR amplification primers used.

| Primer | Sequence |
|---|---|
| *B. subtilis* secY forward | CGC<u>CCATGG</u>TTAAAAACAATCTCCAACTTTATGCG (SEQ ID No:9)<br>NcoI |
| *B. subtilis* secY reverse | CGC<u>GTCGAC</u>TTAGTTTTTCATAAATCCACGGTA (SEQ ID No:10)<br>ClaI |
| *B. subtilis* secE forward | GGG<u>ATCGAT</u>GGAGGTTTTAATTCATGCGTATTATGAAA (SEQ ID No:11)<br>ClaI |
| *B. subtilis* secE reverse | CGC<u>GGATCC</u>TCATTATTCAACTATTAA (SEQ ID No:12)<br>BamHI |
| *B. subtilis* YvaL forward | AAA<u>GGATCC</u>TAGTCTGGAGGTGTATGGATGC (SEQ ID No:13)<br>BamHI |
| *B. subtilis* yvaL reverse | AAA<u>TCTAGA</u>TTCTCGAGCCCTATAGGATATAAGCAAGC (SEQ ID No:14)<br>XbaI |
| *E. coli* secG forward | CCC<u>GGATCC</u>GGAGGTTTTAATTCATGTATGAAGCTCTTT (SEQ ID No:15)<br>BamHI |
| *E. coli* secG reverse | CCC<u>TCTAGA</u>CTCGAGTTAGTTCGGGATATCGC (SEQ ID No:16)<br>XbaI |
| *B. subtilis* phoB forward | GGG<u>CCATGG</u>GAAAAAAATTCCCAAAGAAA (SEQ ID No:17)<br>NcoI |
| *B. subtilis* phoB reverse | GGG<u>GGATCC</u>TTACTTATCGTTAATCTTAAT (SEQ ID No:18)<br>BamHI |

Recognition sites of restriction enzymes used are underlined. Ribosome-binding sites, and start and stop codons are indicated in bold.

1984, Applied Environmental Microbiology 48: 726–731) based broad host range vector containing the lactococcus derived p32 promotoer (van der Vossen et al., 1987, Applied and Environmental Microbiology 10:2452–2457) with synthetic ribosome binding site and NcoI site overlapping the start codon. The *B. amyloliquefaciens* α-amylase gene was isolated by PCR from plasmid pKTH10 (Palva, 1982, Gene 1:81–87) as an NcoI-BamHI cassette, and ligated into NcoI-BamHI digested pAMP21. The resulting vector, named pET468, harbors the amyQ gene under control of the constitutive p32 promoter. Vectors pET472 and pET473 were generated by ligating the *E.coli* and *B. subtilis* secG genes, respectively, containing BamHI-BssHII fragments from the pBluescript derivatives into BamHI-BssHII-MluI digested pET468. Resulting vectors express *B. amyloliquefaciens* α-amylase and secG or yvaL as a tandem operon from the single p32 promoter.

A vector for the disruption of yvaL was generated as follows. The regions immediately upstream and downstream of the yvaL were amplified from chromosomal DNA from strain DB104 as BamHI-XbaI and KpnI-HincII cassettes respectively, and cloned into pBluescript SK+. Subsequently a BglII-PvuII digested chloramphenicol resistance marker was placed between the BamHI and HincII sites, yiedling pDELG2. This vector contains the chromosomal region as is present in DB104 with the yvaL replaced by the chloramphenicol resistance marker.

Plasmid pET812 containing a synthetic operon of *Bacillus subtilis* secY, secE and *E. coli* secG, and plasmid pET822 containing secY, and secE and yvaL of *B. subtilis* were constructed for expression in *E. coli* as described before (Van der Does et al., 1996) using the primers listed in Table 1.

TABLE 2

List of plasmids used in this study.

| name: | replicon | resistance | relevant expression |
|---|---|---|---|
| pDELG2 | ColE1 | Amp. Cam | — (deletion vector) |
| pPR111 | ColE1. repR | Amp. Phleo | — |
| pET302 | pBR | Amp | — |
| pET304 | pBR | Amp | *E. coli* SecG |
| pET324 | pBR | Amp | — |
| pET461 | pBR | Amp | *B. subtilis* PhoB (his-tagged) |
| pET470 | ColE1. repR | Amp. Phleo | *E. coli* SecG |
| pET471 | ColE1. repR | Amp. Phleo | *B. subtilis* YvaL |
| pET468 | repA | Ery | α-amylase |
| pET472 | repA | Ery | α-amylase *E. coli* SecG |
| pET473 | repA | Ery | α-amylase *B. subtilis* YvaL |
| pET812 | pBR | Amp | *B. subtilis* SccYE |
| pET820 | pBR | Amp | *B. subtilis* YvaL |
| pET822 | pBR | Amp | *B. subtilis* SccYE-YvaL | c. Deletion of SecG from the Chromosome of *B.subtilis*

Vector pDELG2 was digested with PvuII to yield a 2.8 kb linear fragment containing the regions flanking the yvaL, which was replaced by a chloramphenicol resistance marker. *B. subtilis* DB104 was transformed with the fragment using natural competence (Young, 1967, Nature 213:773–775), and chloramphenicol resistant colonies were selected. The correct position of the chromosomal replacement was confirmed by PCR. In the resulting strain, DB104ΔG, the yvaL has been replaced by the chloramphenicol resistance gene while leaving the flanking regions intact.

d. Growth Experiments

*B. subtilis* DB104 and DB104ΔG were transformed with each of six plasmids constructed for testing, ie. pPR111, pET470, pET471, pET468, pET472 and pET473. After transformation, plates were incubated at 30° C. overnight. Selective pressure using the appropriate antibiotics was applied from this point onwards. No chloramphenicol was used at this stage. A single colony was picked for each transformant and cultured overnight at 30° C. in liquid medium. 5 μl of the overnight culture were struck on plates and incubated at temperatures ranging from 15° C. to 30° C. until the colonies of the wild-type strain reached a diameter of several millimeters. Plates were inspected daily and the occurrence and size of the colonies were noted.

For expression in E. Coli plasmids pET820 and pET304 were transformed to E. coli KN370 (ΔsecG::kan) as described before (Nishiyama et al., 1994, The EMBO Journal 13:3272–3277) and assay for the formation of single colonies on agar-plates at either 20° C. or at 37° C., with or without induction using 1 PTG (1 mM).

e. Analysis of Secreted Proteins

B. subtilis DB104 and DB104ΔG transformed with plasmid pET468 were grown overnight at 30° C. in liquid medium. The cultures were cooled on ice and fractionated into a cellular fraction and culture medium by centrifugation. Alternatively, the overnight cultures were diluted 1:50 into fresh medium, grown to an $OD_{600}$ of 0.6 and incubated overnight at 15° C. The culture supernatant was precipitated with 10% w/v TCA, washed twice with cold acetone and analysed by SDS-PAGE. Cellular pellets of the cultures were resuspended in sample buffer, sonicated and analysed by SDS-PAGE. For further analysis of the cellular fractions, accessibility for proteinase K was tested. Transformed DB104 and DB104ΔG were grown overnight at 30° C. and harvested by centrifugation. The cellular pellet was washed once with TN (50 mM TRIS-Cl, pH 7.5, 100 mM NaCl) buffer, and resuspended in the same buffer containing 0.5 mg/ml lysozyme. After incubation for 15 min. on ice, proteinase K was added to a final concentration ranging from 0 to 2 mg/ml and the suspension was incubated for further 15 min. Finally, the suspension was precipitated with TCA, washed with acetone and analysed by SDS-PAGE.

f. Expression of pET812 and pET822 and Preparation of Inside Out Vesicles

E. coli SF100 was used for the overexpression of B. subtilis SecY. SecE, and either SccG of E. coli (pET812) or YvaL of B. subtilis (pET822). Expression of the proteins and isolation of inside out vesicles was performed as described before (Van der Does et al., 1996).

g. E.coli SecA Stripping of the Vesicles and In Vitro Translocation

To remove the E. coli SecA from the inside out vesicles 100 μl of vesicles (10 mg/ml) were incubated with 50 μl of polyclonal antibody directed against E. coli SecA (Schiebel et al., 1991, Molecular Microbiology 22: 619–629). In vitro translocation of $^{125}$I-labeled his-prePhoB(Van Wely et al., 1998, European Journal of Biochemistry) into inner membrane vesicles was assayed as described before (Cunningham, et al., 1989, Van Der Does et al., 1996) except that purified B. subtilis SecA (Van der Wolk et al., 1993, Molecular Microbiology 8:31–42) was used instead of E. Coli SecA (0.5 μg).

h. Production of B. Subtilis SecG Polyclonal Antibody

A peptide polyclonal antibody directed against the internal YvaL sequence Tyr-Ala-Glu-Gln-Leu-Phe-Gly-Lys-Gln-Lys-Ala-Arg-Gly-Leu-Asp (SEQ ID No:19) coupled to KLH via the tyrosine residue was produced in Rabbits according to standard procedures by NEOSYSTEM, Strasbourg, France.

EXAMPLE II

This Example illustrates that B.subtilis SecG is a functional homolog of E.coli SecG.

The membrane vesicle derived from cells expressing pET812 and pET822 were stripped of their indigenous E.coli SecA using a polyclonal antibody directed against SecA and subjected to an in vitro translocation assay using $^{125}$I-labeled his-prePhoB. In FIG. 8, the result of the translocation is shown. When no B. subtilis SecA is added both vesicles containing either SecYEG or SecYE and YVAL show only little background translocation. However, when B.subtilis SecA is added to vesicles containing SecYE and YVAL, an enormous increase in translocation efficiency of $^{125}$I-prePhoB is observed, while in the vesicles containing the SecYE and E.coli SecG no extra translocation is observed. From these data, it can be concluded that B.subtilis SecYE together with B.subtilis Yval and SecA forms a functional preprotein translocase that mediates the translocation of Bacillus prePhoB protein in vitro.

EXAMPLE III

This example illustrates that B.subtilis SecY, SecE and SecG (YVAL) proteins can be overexpressed in E.coli.

To establish whether the pET812 and pET 822 are expressed in E.coli SF100, inside out vesicles were analyzed on a 15% SDS-PAGE. Both the SecY and SecE of B.subtilis were readily visible on a commassie stained gel (FIG. 7A). The B.subtilis SecG and increased amounts of E.coli SecG could be detected on an immunoblot using antibodies directed against these proteins (FIGS. 7B–7C).

EXAMPLE IV

This example illustrates the involvement of protein secretion machinery in the secretion of proteins for wild type cells and cells having a deletion in B.subtilis SecG.

In the culture supernatants of cells grown at different temperatures, no differences between wild type and mutant cells was observed (FIG. 6A). The cellular fraction, showed some differences in the banding pattern. The difference mainly concerns the absence. of some bands in the mutant. The localization of these proteins was determined by breakdown of the cell wall by lysozyme and subsequent protease digestion of the accessible proteins (FIG. 6B). Some of the protein bands are digested already by low concentrations of proteinase K, whereas breakdown of most other proteins only occurs after disruption of the cell membrane by Triton X-100. These proteins appear to be secreted. Some of these secreted proteins are absent in the mutant strain. Therefore, the B.subtilis SecG disruption mutant appears to be defective in the secretion of some extracellular proteins.

EXAMPLE V

This example illustrates the effect of a SecG deletion on cell growth.

Disruption of the E.coli secG gene has been shown to result in a cold-sensitive phenotype (Nishiyama et al., 1994, EMBO Journal 13:3272–3277), at non-permissive temperatures of 25° C. and below. Deletion of B.subtilis secG from the chromosome did not result in any phenotype when cells were grown at 37° C. either on rich or minimal media. Incubations below 20° C. demonstrated a mild cold sensitivity, where the DB104ΔG strain showed progressively slower growth as compared to DB104. The mutant strain didn't stop growing completely, however. Compared to the wild type, growth is retarded more severely when temperatures are lowered further. After shifting the cells again to higher temperatures, growth resumed at a faster rate.

Cells were transformed with plasmids expressing *E.coli* SecG or *Bacillus subtilis* SecG as well as a control plasmid. After preincubation at temperatures that do not affect growth of the mutant, cells were plated and incubated at several lower temperatures. Growth of the colonies was monitored over a period of several days. Wild type and mutant cells transformed with the control plasmid behaved like the non-transformed counterparts, showing retarded growth but not a complete stop at lower temperatures. Transformation of the mutant with pET471 expressing the secG gene product could relieve the retardation, showing that the phenotype of the mutant was not caused by any polar effects but by the deletion of secG itself. Surprisingly, when the mutant is transformed with pET470 expressing *E.coli* SecG, growth is stopped completely at temperatures of 20° C. or less. When the same plasmid is brought into the wild type cells, some interference with growth is observed at lower temperatures but not at 25° C. A disruption of the secG gene renders *Bacillus subtilis* mild cold-sensitive, but is not an essential gene for *B.subtilis*. The results are presented in Table 3.

TABLE 3

Results of the growth experiments

| | | growth at: | | |
|---|---|---|---|---|
| strain: | expression | 15° C. | 20° C. | 25° C. |
| DB104::111 | — | ++ | ++ | ++ |
| DB104::470 | *E. coli* SecG | ± | ± | ++ |
| DB104::471 | *B. sub* YvaL | ++ | ++ | ++ |
| ΔyvaL::111 | — | ± | ± | ++ |
| ΔyvaL::470 | *E. coli* SecG | – | – | ++ |
| ΔyvaL::471 | *B. sub* YvaL | ++ | ++ | ++ |
| DB104::468 | α-amylase | ++ | ++ | ++ |
| DB104::472 | α-amylase *E. coli* SecG | ± | ± | ++ |
| DB104::473 | α-amylase *B. sub* YvaL | ++ | ++ | ++ |
| ΔyvaL::468 | α-amylase | – | – | ++ |
| ΔyvaL::472 | α-amylase *E. coli* SecG | ± | ± | ± |
| ΔyvaL::473 | α-amylase *B. sub* YvaL | ± | ± | ± |

++, growth like reference; ±, growth, but slower than reference; –, no growth.

EXAMPLE VI

This example illustrates the effect of expression of a secretory protein.

*B. subtilis* cells mutant in secG and wild type cells were transformed with plasmid pET468 and derivatives. These plasmids expression alpha-amylase thereby invoking secretory stress. Derivatives of pET472 and pET473 express alpha amylase in combination with *E.coli* SecG or *B.subtilis* SecG, respectively. Expression of alpha amylase did not retard growth of the deletion mutant at 30° C., the temperature used for preculturing the cells. At this temperature, the halos that are formed by the alpha amylase on starch containing plates by transformants of wild type and deletion mutants are the same size. When pET468 transformants of the deletion mutant were shifted to lower temperatures, a clear and complete cold sensitivity was demonstrated. Already at 20° C., cells stopped growing completely. When the cells were transformed back to the permissive temperature of 30° C., after prolonged incubation at 20° C., growth was not resumed. The deletion mutant is capable of sustaining a basic level of secretion even at lower temperatures, but cannot handle overexpression of a secreted protein over a broad temperature range.

EXAMPLE VII

Detection of Gram-postive Microorganisms

The following example describes the detection of gram-positive microorganism SecG.

DNA derived from a gram-positive microorganism is prepared according to the methods disclosed in Current Protocols in Molecular Biology, Chap. 2 or 3. The nucleic acid is subjected to hybridization and/or PCR amplification with a probe or primer derived from SecG. A preferred probe comprises the nucleic acid section containing conserved amino acid sequences The nucleic acid probe is labeled by combining 50 pmol of the nucleic acid and 250 mCi of [gamma $^{32}$p] adenosine triphosphate (Amersham, Chicago Ill.) and T4 polynucleotide kinase (DuPont NEN®, Boston Mass.). The labeled probe is purified with Sephadex G-25 superfine resin column (Pharmacia). A portion containing $10^7$ counts per minute of each is used in a typical membrane based hybridization analysis of nucleic acid sample of either genomic or cDNA origin.

The DNA sample which has been subjected to restriction endonuclease digestion is fractionated on a 0.7 percent agarose gel and transferred to nylon membranes (Nytran Plus, Schleicher & Schuell, Durham N.H.). Hybridization is carried out for 16 hours at 40 degrees C. To remove nonspecific signals, blots are sequentially washed at room temperature under increasingly stringent conditions up to 0.1×saline sodium citrate and 0.5% sodium dodecyl sulfate. The blots are exposed to film for several hours, the film developed and hybridization patterns are compared visually to detect polynucleotide homologs of *B.subtilis* SecG. The homologs are subjected to confirmatory nucleic acid sequencing. Methods for nucleic acid sequencing are well known in the art. Conventional enzymatic methods employ DNA polymerase Klenow fragment, SEQUENASE® (US Biochemical Corp, Cleveland, Ohio) or Taq polymerase to extend DNA chains from an oligonucleotide primer annealed to the DNA template of interest.

Various other examples and modifications of the foregoing description and examples will be apparent to a person skilled in the art after reading the disclosure without departing from the spirit and scope of the invention, and it is intended that all such examples or modifications be included within the scope of the appended claims. All publications and patents referenced herein are hereby incorporated in their entirety.

What is claimed is:

1. An expression vector comprising a nucleic acid sequence encoding a secretion factor G (SecG) protein, wherein said secretion factor G is under the control of an expression signal capable of expressing said secretion factor in a gram-positive microorganism, and wherein said nucleic acid sequence comprises SEQ ID NO:1.

2. The expression vector of claim 1, wherein said gram-positive microorganism is a member of the genus Bacillus.

3. The expression vector of claim 2, wherein said Bacillus is selected from the group consisting of *B. subtilis, B. licheniformis, B lentus, B. brews, B. stearothermophilus, B. alkalophilus, B. amyloliquefaciens, B. coagulans, B. circulans, B. lautus,* and *Bacillus thuringiensis*.

4. A gram positive microorganism comprising the expression vector of claim 1.

5. The gram positive microorganism of claim 4, wherein said microorganism is a member of the genus Bacillus.

6. The microorganism of claim 5, wherein said Bacillus is selected from the group consisting of *B. subtilis, B. licheniformis, B. lentus, B. brevis, B. stearothermophilus, B. alcalophilus, B. amyloliquefaciens, B. coagulans, B. circulans, B. lautus,* and *Bacillus thuringiensis*.

7. The microorganism of claim 4, wherein said microorganism further expresses a heterologous protein.

8. The microorganism of claim 7, wherein said heterologous protein is selected from the group consisting of hormones, enzymes, growth factors, and cytokines.

9. The microorganism of claim 8, wherein said heterologous protein is an enzyme.

10. The microorganism of claim 9, wherein said enzyme is selected from the group consisting of proteases, cellulases, amylases, carbohydrases, lipases, reductases, isomerases, epimerases, tautomerases, transferases, kinases and phosphatases.

11. A method of secreting a protein in a gram-positive microorganism according to claim 4 comprising:

a) obtaining a gram-positive microorganisms comprising:
(i) an expression vector comprising a nucleic acid sequence encoding a secretion factor G (SecG) protein, wherein said nucleic acid sequence comprises the sequence set forth in SEQ ID NO:1 and wherein said nucleic acid sequence is under the control of an expression signal capable of expressing SecG in a gram-positive microorganism and
(ii) a nucleic acid sequence encoding said protein to be secreted and;

b) culturing said microorganism under conditions suitable for expression of SecG and expression and secretion of said protein.

12. The method of claim 11, wherein said gram-positive microorganism further comprises a nucleic acid sequence encoding at least one additional secretion factor selected from the group consisting of secretion factor Y (SecY), secretion factor E (SecE), and secretion factor A (SecA).

13. The method of claim 11, wherein said gram-positive mincroorganism is a member of the genus Bacillus.

14. The method of claim 13, wherein said Bacillus is selected from the group consisting of *B. subtilis, B. licheniformis, B. lentus, B. brevis, B. stearothermophilus, B. alcalophilus, B. amyloliquefaciens, B. coagulans, B. circulans, B. lautus,* and *Bacillus thuringiensis*.

15. The method of claim 13, wherein said Bacillus expresses at least one heterologous protein selected from the group consisting of hormones, enzymes, growth factors, and cytokines.

16. The method of claim 15, wherein said heterologous protein is an enzyme.

17. The method of claim 16, wherein said enzyme is selected from the group consisting of proteases, cellulases, amylases, carbohydrases, lipases, isomerases, racemases, epimerases, tautomerases, mutases, transferases, kinases, and phosphatases.

* * * * *